(12) United States Patent
Thurmond et al.

(10) Patent No.: US 7,026,132 B2
(45) Date of Patent: Apr. 11, 2006

(54) METHOD OF MONITORING THE EFFECT OF CATHEPSIN S INHIBITORS

(75) Inventors: Robin Thurmond, San Diego, CA (US); Siquan Sun, San Diego, CA (US); Lars Karlsson, La Jolla, CA (US)

(73) Assignee: Ortho-McNeil Pharmaceutical, Inc., Raritan, NJ (US)

( * ) Notice: Subject to any disclaimer, the term of this patent is extended or adjusted under 35 U.S.C. 154(b) by 417 days.

(21) Appl. No.: 09/938,941

(22) Filed: Aug. 24, 2001

(65) Prior Publication Data

US 2002/0028435 A1 Mar. 7, 2002

Related U.S. Application Data

(60) Provisional application No. 60/230,484, filed on Sep. 6, 2000.

(51) Int. Cl.
*G01N 33/53* (2006.01)

(52) U.S. Cl. .............................. 435/7.92; 435/2; 435/3; 435/4; 435/7.2; 435/7.21; 435/7.23; 435/7.24; 435/40.5; 435/287.2; 435/326; 435/335; 435/372.1; 435/372.3; 435/962; 436/501; 436/506; 436/507; 436/546; 436/63; 436/64; 436/172; 436/175; 436/177; 436/811; 436/813; 436/825; 356/300; 356/326; 356/328; 382/133; 382/141; 382/260

(58) Field of Classification Search ................ 435/7.1, 435/7.2, 7.24, 184, 212, 377, 287.2, 7.21, 435/2, 3, 4, 7.23, 7.92, 29, 40.5, 326, 288.3, 435/288.4, 335, 372.1, 372.3, 962; 436/507, 436/63, 177, 811, 501, 506, 64, 172, 175, 436/546, 809, 813, 825; 356/300, 326, 328; 382/133, 141, 260

See application file for complete search history.

(56) References Cited

U.S. PATENT DOCUMENTS

| 5,919,639 | A | 7/1999 | Humphreys et al. |
| 5,976,858 | A | 11/1999 | Palmer et al. |
| 6,245,904 | B1 | 6/2001 | Melms et al. |
| 6,495,333 | B1 * | 12/2002 | Willmann et al. ......... 435/7.24 |

FOREIGN PATENT DOCUMENTS

| WO | WO 97/40066 | 10/1997 |
| WO | WO 99/58153 | * 11/1999 ................ 435/7.24 |

OTHER PUBLICATIONS

Nakagawa et al., "Impaired Invariant Chain Degradation and Antigen Presentation and Diminished Collagen-Induced Arthritis in Cathepsin S Null Mice", *Immunity* (1999) 10:207-217.

(Continued)

*Primary Examiner*—Long V. Le
*Assistant Examiner*—Gailene R. Gabel

(57) ABSTRACT

The present invention relates to a method for monitoring the effect of in vivo administration of Cathepsin S inhibitors by measuring accumulation of an intermediate degradation product of invariant chain (Ii), in particular the p10 Ii fragment, in blood of dosed subjects.

3 Claims, 1 Drawing Sheet

Invariant Chain Degradation in PCBMs

← p10Ii

OTHER PUBLICATIONS

Palmer et al., "Vinyl Sulfones as Mechanism-Based Cysteine Protease Inhibitors", *J. Med. Chem.* (1995) 38:3193.

Riese et al., "Essential Role for Cathepsin S in MHC Class II-Associated Invariant Chain Processing and Peptide Loading", *Immunity* (1996) 4(4):357-366.

Riese et al., "Cathepsin S Activity Regulates Antigen Presentation and Immunity", *J. Clin. Invest.* (1998) 101(11): 2351-2363.

Shi et al., "Cathepsin S Required for Normal MHC Class II Peptide Loading and Germinal Center Development", *Immunity* (1999) 10:197-206.

Shi et al., "Role For Cathepsin F In Invariant Chain Processing And Major Histocompatibility Complex Class II Peptide Loading By Macrophages", *J. Exp. Med.*, vol. 191(7), pp. 1177-1185 (2000).

Chapman, "Endosomal Proteolysis And MHC Class II Function", *Curr. Op. Immunol.*, vol. 10, pp. 93-102 (1998).

Thurmond et al., "Identification Of A Potent And Selective Noncovalent Cathepsin S Inhibitor", *J. Pharmacol. Exp. Ther.*, vol. 308, pp. 268-276 (2004).

Villadangos et al., "Degradation Of Mouse Invariant Chain: Roles Of Cathepsins S And D And The Influence Of Major Histocompatibility Complex Polymorphism", *J. Exp. Med.*, vol. 186, No. 4, pp. 549-560 (1997).

* cited by examiner

Invariant Chain Degradation in PCBMs

METHOD OF MONITORING THE EFFECT OF CATHEPSIN S INHIBITORS

CROSS-REFERENCE TO RELATED APPLICATION

This application claims the benefit of U.S. Provisional Application Ser. No. 60/230,484, filed Sep. 6, 2000.

FIELD OF THE INVENTION

The present invention relates to a method for monitoring the effect of in vivo administration of Cathepsin S inhibitors by measuring accumulation of an intermediate degradation product of invariant chain (Ii), in particular the p10 Ii fragment, in blood of dosed subjects.

BACKGROUND OF THE INVENTION

The recognition of antigen-presenting MHC class II molecules by CD4$^+$ T cells is a crucial component of the immunological response. Class II molecules, like other transmembrane proteins, are translocated into the endoplasmic reticulum after synthesis, where they associate with a third protein, the invariant chain (Ii). This molecule is a type II transmembrane protein that serves as a class II-specific chaperone which promotes the exit of class II-Ii complexes from the endoplasmic reticulum and prevents class II molecules from binding peptides and unfolded proteins in the endoplasmic reticulum and in the secretory pathway.

A targeting motif in the cytoplasmic tail of Ii directs the complexes from the secretory pathway into the endosomal system. Before the MHC class II molecules can present antigen the Ii must be removed. This is accomplished by a series of proteases that break Ii down into small peptides. However, an Ii fragment, called class II-associated invariant chain peptide (CLIP), which occupies the peptide-binding groove of the class II molecule, is in most cases not spontaneously released. The CLIP fragment serves as a substitute peptide that protects the class II binding pocket from collapsing both during intracellular transport and after Ii degradation in the endosomal system. Binding of antigenic peptides, generated from endocytosed proteins, requires an empty, yet open binding site, and therefore CLIP has to be released while the open binding site needs to be stabilized to allow the binding of other peptides. Human Leukocyte Antigen DM ('HLA-DM') has been well documented to mediate both of these functions, thus promoting the binding of antigenic peptides. After acquiring peptides, the class II molecules are transported to the cell surface via routes that are largely unknown.

Blocking the presentation of antigens is a promising way to inhibit the immune response. This could be done by disrupting the uptake, the proteolytic processing, or binding to MHC class II molecules. Blocking the uptake may be problematic since many different cell types require this function. Inhibition of the proteolytic processing of particular antigens may be of use since different proteases may be involved in cleaving different antigens, however these proteases are not specific and may lead to other side-effects. One way to specifically block the binding to the antigens to the MHC class II is to inhibit the proteolysis of the invariant chain. If this is not removed then the MHC class II molecules cannot be loaded with peptides, hence blocking Ii degradation would decrease antigen presentation to CD4+ T-cells and disrupt the normal immune response.

Cathepsin S (CatS) is a cysteine protease expressed in lymphatic tissues. It is has been identified as playing a major role in invariant chain proteolysis which is a prerequisite for peptide loading of MHC class II (Riese et al. (1996) Immunity 4:357). It has 50–60% identity to cathepsins L and K, but differs in that it has a broad pH optimum that extends to alkaline pH. Inhibitors have been shown in animal models to modulate antigen presentation and are effective in an asthma model (Riese et al., *J. Clin. Invest.* (1998) 101:2351). Mice deficient in cathepsin S have an impaired ability to present exogenous proteins by professional antigen presenting cells (Nakagawa et al., *Immunity* (1999) 10:207; Shi et al., *Immunity* (1999) 10:197).

Compounds that inhibit the proteolytic activity of human cathepsin S are expected to find utility in the treatment of chronic autoimmune diseases including, but not limited to, lupus, rheumatoid arthritis, and asthma; and have potential utility in modulating the immune response to tissue transplantation.

Methods of modulating autoimmunity with an agent that modulates cathepsin S activity, e.g. proteolysis of the Ii chain, as well as methods of treating a subject having an autoimmune disorder, methods of evaluating a treatment for its ability to modulate an immune response are described in WO 99/58153.

SUMMARY OF THE INVENTION

The present invention concerns a method of or an assay for monitoring the effect of in vivo administration of a cathepsin S inhibitor, said method or assay comprising:
(a) taking a blood sample of the subject treated;
(b) measuring the accumulation of an intermediate degradation product of invariant chain (Ii) in said blood sample.

More in particular said method comprises:
(a) taking a blood sample of the subject treated;
(b) purifying the white blood cells from said sample;
(c) making whole cell lysates of the purified white blood cells;
(d) analyzing the lysates for presence of an intermediate degradation product of invariant chain (Ii) by a suitable assay method.

Suitable assay methods comprise for example Western blot assay or ELISA assay methods. A particular intermediate degradation product of invariant chain (Ii) is p10Ii. In a further aspect, the invention concerns a test kit comprising materials suitable for conducting the above methods or assays.

DETAILED DESCRIPTION OF THE INVENTION

Figure 1:
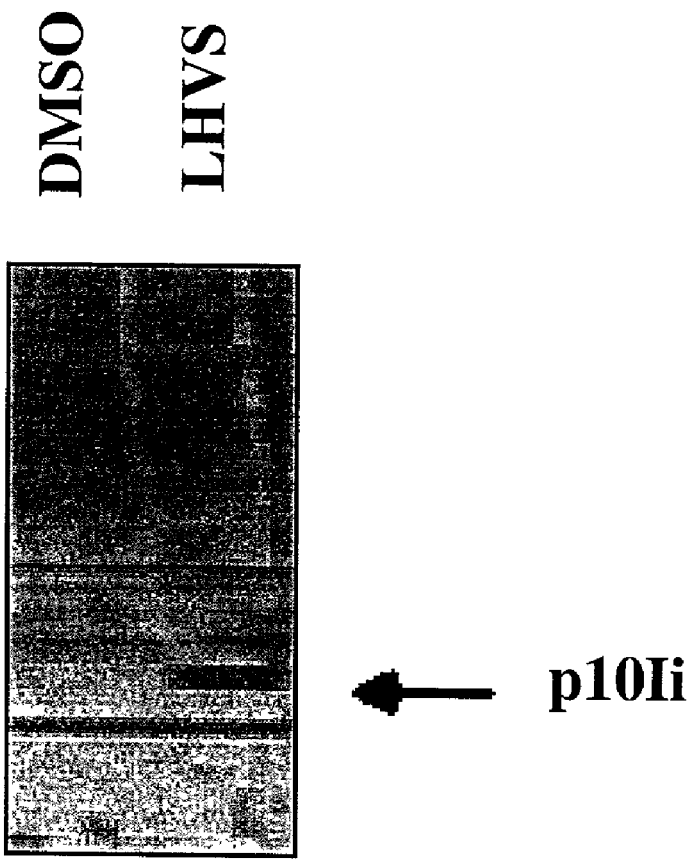
FIG. 1: In the presence of LHVS, the presence of p10Ii fragment is easily seen.

Thus the present invention provides a method for monitoring the effect of in vivo administration of Cathepsin S inhibitors, by measuring accumulation of an intermediate degradation product of invariant chain (Ii), i.e. the p10Ii fragment, in blood of dosed subjects.

The said assay of the present invention is particularly useful in a clinical trial setting. However it can also be applied to monitor the effect of Cathepsin S inhibitors in vivo in animal studies, which include but are not limited to monkey, dog, pig, rabbit, guinea pig, and rodents.

The effect of in vivo administration of Cathepsin S inhibitors, in a clinical trial setting, can be monitored by measuring accumulation of an intermediate degradation product of invariant chain (Ii), i.e. the p10Ii fragment, in blood of dosed subjects.

Briefly, after administration of Cathepsin inhibitors for a certain period of time, preferably 16–30 hr, blood is drawn and white blood cells are purified, e.g. either by lysis of red blood cells or by a FICOLL gradient centrifugation. Whole cell lysates of WBC are then made and then analyzed by either a Western blot assay or a ELISA assay. For Western assay, cell lysates are first resolved on PAGE gels. After transferring to nitrocellulose membrane, Ii and its intermediate degradation products, including the p10Ii, can then be detected using a mouse mAb against Ii, e.g. Pin1.1, or a rabbit polyclonal antibody against the entire Ii or a peptide fragment. For ELISA assay, a pair of antibodies against Ii, including Pin1.1 and a rabbit polyclonal antibody against C-terminal of p10Ii, can be used.

The said assay can also be applied to monitor effect of Cathepsin S inhibitors in vivo in animal studies, which include but not limit to monkey, dog, pig, rabbit, guinea pig and rodents.

The advantage of the invention is that the method is simple and considered more reliable in determining in vivo efficacy of Cathepsin inhibitor compounds.

The method can be used to assay the efficacy of Cathepsin inhibitory compounds not only in an experimental screening or clinical setting. It is also useful to monitor patients who have been treated with Cathepsin inhibitors to check efficacy of their treatment and to adjust dosing where necessary. This will allow the prescribing or supervising physician to more precisely and effectively dose the desired cathepsin S inhibitory drug regimen.

EXAMPLE 1

Monitoring Cathepsin S Inhibition in Human Blood

The effect of in vivo administration of Cathepsin S inhibitors, in a clinical trial setting, can be monitored by measuring accumulation of an intermediate degradation product of invariant chain (Ii), i.e. the p10Ii fragment, in blood of dosed subjects. Briefly, after administration of Cathepsin inhibitors for a certain period of time, preferably 16–30 hr, blood is drawn and white blood cells are purified, e.g. either by lysis of red blood cells or by a FICOLL gradient centrifugation. Whole cell lysates of WBC are then made and analyzed by either a Western blot assay or an ELISA assay. For Western assay, cell lysates are first resolved on SDS-PAGE gels. After transferring to nitrocellulose membrane, Ii and its intermediate degradation products, including the p10Ii, can then be detected using a mouse mAb against Ii, e.g. Pin1.1 or rabbit polyclonal antibodies specific for the C-terminal of the p10Ii fragment. For ELISA assay, a pair of antibodies against Ii, including Pin1.1 and a rabbit polyclonal antibody against C-terminal of p10Ii, can be used. The same assay can also be applied to monitor effect of Cathepsin S inhibitors in vivo in animal studies, for example in monkeys, dogs, pigs, rabbits, guinea pigs, and rodents.

In the present example purified peripheral blood mononuclear cells from human blood were incubated with the cathepsin S inhibitor, LHVS (morpholinurea-leucine-homophenylalanine-vinylsulfonephenyl, also referred to as 4-morpholinecarboxamide, N-[(1S)-3-methyl-1-[[[(1S,2E)-1-(2-phenylethyl)-3-(phenylsulfonyl)-2-propenyl]amino]carbonyl]butyl]-(9C1)). This compound has been described in U.S. Pat. No. 5,976,858 and in Palmer et al., *J. Med. Chem.* (1995) 38:3193 and Riese et al., *Immunity* (1996) 4:357. After incubation for 24 hours, the samples were run using standard SDS-PAGE protocols, transferred to nitrocellulose membranes and probed with an antibody which recognizes the invariant chain including the p10Ii fragment. In the presence of LHVS the p10Ii fragment can easily be seen (FIG. 1). This represents a block in the degradation of Ii due to inhibition of cathepsin S.

What is claimed is:

1. A method of monitoring the effect of in vivo administration of a cathepsin S inhibitor to a subject, comprising the steps of:
   a) taking a blood sample of the subject;
   b) purifying the white blood cells from said sample;
   c) making whole cell lysates of the purified white blood cells; and
   d) analyzing the lysates for presence of a p10Ii fragment of invariant chain (Ii) by a suitable assay method, wherein the presence of said p10Ii fragment represents a block in degradation of the invariant chain due to inhibition of cathepsin S resulting from the in vivo administration of the cathepsin S inhibitor.

2. A method of monitoring the effect of in vivo administration of a cathepsin S inhibitor to a subject as defined in claim 1 wherein the suitable assay method in step (d) is Western blotting or enzyme-linked immunosorbent assay.

3. A method of monitoring the effect of in vivo administration of a cathepsin S inhibitor to a subject as defined in claim 1 wherein the subject is a human.

* * * * *